(12) United States Patent  (10) Patent No.: US 9,257,038 B2
Weintraub et al.  (45) Date of Patent: *Feb. 9, 2016

(54) FLUIDS TESTING APPARATUS AND METHODS OF USE

(71) Applicant: Labstyle Innovation Ltd., Caesarea (IL)

(72) Inventors: David Weintraub, Yavne (IL); Oren Fuerst, Ramat Hasharon (IL); Dov Oppenheim, Jerusalem (IL); Eyal Cohen, Gedera (IL); Meir Plevinski, Tel Aviv (IL)

(73) Assignee: LABSTYLE INNOVATION LTD., Ramat-Gan (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/815,357

(22) Filed: Jul. 31, 2015

(65) Prior Publication Data

US 2015/0339918 A1  Nov. 26, 2015

Related U.S. Application Data

(63) Continuation of application No. 14/450,621, filed on Aug. 4, 2014, now Pat. No. 9,125,549, which is a continuation of application No. 14/176,627, filed on Feb. 10, 2014, now Pat. No. 8,797,180, which is a (Continued)

(51) Int. Cl.
*G08C 19/22* (2006.01)
*G08C 19/00* (2006.01)
(Continued)

(52) U.S. Cl.
CPC .............. *G08C 19/00* (2013.01); *A61B 5/0004* (2013.01); *A61B 5/14532* (2013.01);
(Continued)

(58) Field of Classification Search
CPC . G08C 19/00; G01N 33/66; G01N 33/48785; G01N 33/487; G01N 33/49; G01N 33/493; H01R 24/58; H01R 2107/00; H01R 2201/20; A61B 5/0004; A61B 5/14532; A61B 2560/045; A61B 2560/0487; A61B 2562/0295; A61B 5/6898
USPC .............. 340/870.07, 870.28, 870.16, 870.11, 340/573.1; 600/300, 316, 347, 365; 128/897, 903, 920; 604/66; 455/575.1, 455/550.1, 572; 73/61.59; 702/2, 32; 705/2, 705/3; 710/15, 16
See application file for complete search history.

(56) References Cited

U.S. PATENT DOCUMENTS 8,145,431 B2 * 3/2012 Kloepfer ................ G01N 21/78
340/539.12
8,797,180 B2 * 8/2014 Weintraub ........... G01N 33/493
340/573.1

(Continued)

*Primary Examiner* — Anh V La
(74) *Attorney, Agent, or Firm* — Greenberg Traurig, LLP

(57) ABSTRACT

The invention is directed to a mobile hand held miniature laboratory system in general, and to fluid testing apparatus for performing a parameter measurement in a fluid sample and methods of use in particular. The apparatus comprising: a strip adapted to absorb a fluid sample and to produce a signal indicative of the parameter level in the sample; and adaptor adapted to connect the strip to a smart phone to allow delivery of the produced signal or a correlated signal to the smart phone for obtaining a measurement of the fluid parameter displayed on the smart phone, wherein the testing apparatus relies on the smart phone at least for power supply and display device. The fluid may be a physiological fluid such as blood, urine, saliva or amniotic fluid, or a non-physiological fluid such as fluid obtained from industrial pools for fish or algae growth, or entertainment swimming pools.

14 Claims, 9 Drawing Sheets

Related U.S. Application Data continuation of application No. 13/946,688, filed on Jul. 19, 2013, now Pat. No. 9,127,711, which is a continuation of application No. 13/697,022, filed as application No. PCT/IL2011/000369 on May 8, 2011.

(60) Provisional application No. 61/431,449, filed on Jan. 11, 2011, provisional application No. 61/332,778, filed on May 9, 2010.

(51) Int. Cl.
*G01N 33/66* (2006.01)
*G01N 33/493* (2006.01)
*G01N 33/487* (2006.01)
*G01N 33/49* (2006.01)
*A61B 5/00* (2006.01)
*H01R 24/58* (2011.01)
*A61B 5/145* (2006.01)
*H01R 107/00* (2006.01)

(52) U.S. Cl.
CPC ....... *G01N 33/487* (2013.01); *G01N 33/48785* (2013.01); *G01N 33/49* (2013.01); *G01N 33/493* (2013.01); *G01N 33/66* (2013.01); *H01R 24/58* (2013.01); *A61B 5/6898* (2013.01); *A61B 2560/045* (2013.01); *A61B 2560/0487* (2013.01); *A61B 2562/0295* (2013.01); *H01R 2107/00* (2013.01); *H01R 2201/20* (2013.01)

(56) References Cited

U.S. PATENT DOCUMENTS 9,125,549 B2 * 9/2015 Weintraub ........... A61B 5/0004
2010/0279418 A1 * 11/2010 Larson .................. C12Q 1/006
436/63

* cited by examiner

FLUIDS TESTING APPARATUS AND METHODS OF USE

FIELD OF THE INVENTION

The present invention is generally related to a novel disposable apparatus adapted to allow the performance of various fluids test in order to measure the level of different parameters in such fluid in general, and to perform various physiological fluids tests such as urine, blood, amniotic fluid, and saliva in particular, in an easy friendly and inexpensive way, by symbiotic relations of a special apparatus with a smart phone ("Symbiotronic" relation).

BACKGROUND ART

The following references may be relevant as background art to the present invention:
U.S. Patent Ap. 20080299009; US2006260940; U.S. Pat. No. 7,810,729; Qi Li, Jingqi Yuan, Proceedings of the 2005 IEEE, Engineering in Medicine and Biology 27th Annual Conference, Shanghai, China, Sep. 1-4, 2005; www.alivet-ec.com, Mobile Diabetes Management; www.entrahealth-systems.com MyGlucoHealth Diabetes App; www.bodytel.com; www.myglucometer.com; www.bayercontourusb us; https://my.glucophone.cornlrunscript.cfm?page=bome.cfm; https://sites.google.cornlsite/glucosemeterandroid; http://www.androlib.com/android.application.com-fjbelchi-glucosemeter-Aqmx.aspx

SUMMARY OF THE INVENTION

This summary section of the patent application is intended to provide an overview of the subject matter disclosed herein, in a form lengthier than an "abstract", and should not be construed as limiting the disclosure to any features described in this summary section.

The present invention is aimed to provide a novel fluid testing apparatus for performing a parameter measurement in a fluid sample comprising: A strip adapted to absorb a fluid sample and to produce a signal indicative of the parameter level in the sample; and an adaptor adapted to connect said strip to a smart phone to thereby allow delivery of the produced signal or a correlated signal to said smart phone for obtaining a measurement of said fluid parameter displayed on said smart phone, wherein said testing apparatus relies on said smart phone at least for power supply and display means.

It is also the aim of the present invention to provide a novel physiological fluid testing apparatus for performing a parameter measurement in a fluid sample comprising: a strip adapted to absorb a physiological fluid sample and to produce a signal indicative of said parameter level in said sample; and an adaptor adapted to connect said strip to a smart phone to thereby allow delivery of the produced signal or a correlated signal to said smart phone for obtaining a measurement of said fluid parameter displayed on said smart phone, wherein said physiological fluid testing apparatus relies on said smart phone at least for power supply and display means.

The present invention is further aimed to provide a blood testing apparatus for performing glucose measurement in a blood sample comprising: a glucose strip adapted to absorb a blood sample and to produce a signal indicative of the glucose level in said blood sample; and an adaptor adapted to connect said glucose strip to a smart phone to thereby allow delivery of the produced signal or a correlated signal to said smart phone for obtaining a measurement of the glucose level displayed on said smart phone, wherein said blood testing apparatus relies on said smart phone at least for a power supply and display means.

The present invention is further directed to a method for performing glucose measurement in a blood sample comprising the steps of: Installing a dedicated application software on a smart phone; Loading a blood sample on a glucose measurement apparatus, said apparatus comprising: a strip adapted to absorb blood sample and to produce a signal indicative of said glucose level in said sample; and an adaptor adapted to connect said strip to a smart phone to thereby allow delivery of the produced signal or a correlated signal to said smart phone for obtaining a measurement of said glucose level displayed on said smart phone, wherein said glucose measurement apparatus relies on said smart phone at least for a power supply and display means; Inserting said loaded glucose measuring apparatus into a headset jack of a smart phone to thereby allow communication between said apparatus and said smart phone and delivery of power supply; and, obtaining the measured glucose level displayed on said smart phone screen.

The present invention further provides a blood glucose monitoring apparatus for determining glucose level in a blood sample of a user comprising: a lancing device adapted to allow said user obtaining a blood sample: a slot adapted to allow collection of said blood sample; a glucose strip adapted to absorb said blood sample and to produce a signal indicative of said glucose level in said sample; an adaptor adapted to functionally connect said glucose strip to a smart phone via a connecting plug designed to be inserted into a headset jack of a smart phone to functionally deliver to said smart phone the produced signal or a correlated signal thereof, and to allow said apparatus obtain at least a power supply and display means from said smart phone.

The invention is further aimed to provide a mobile miniature laboratory system capable of performing fluid parameter measurement of a sample, said system comprising: A smart phone installed with a dedicated application software; A strip adapted to absorb a fluid sample and to produce a signal indicative of said parameter level in said sample; An adaptor adapted to connect said strip to a smart phone to thereby allow delivery of the produced signal or a correlated signal to said smart phone for obtaining a measurement of said fluid parameter displayed on said smart phone, wherein said testing apparatus relies on said smart phone at least for a power supply and display means.

BRIEF DESCRIPTION OF THE DRAWINGS

It should be clear that the description of the embodiments and attached Figures set forth in this specification serves only for a better understanding of the invention, without limiting its scope. It should also be clear that a person skilled in the art, after reading the present specification could make adjustments or amendments to the attached Figures and above described embodiments that would still be covered by the present invention. In the figures, identical structures, elements or parts that appear in more than one figure are generally labeled with the same numeral in all the figures in which they appear. Dimensions of components and features shown in the figures are generally chosen for convenience and clarity of presentation and are not necessarily shown to scale. Many of the figures presented are in the form of schematic illustrations and, as such, certain elements may be drawn greatly simplified or not-to-scale, for illustrative clarity. The figures are not intended to be production drawings. The figures (Figs.) are listed below.

FIG. 4A is an upper front view illustration of PFTA 400 in a packed form made of two subunits; FIG. 4B is an upper front view of first subunit 402 of PFTA 400; FIG. 4C is an upper front view of second subunit 404 of PFTA 400.

DETAILED DESCRIPTION OF PREFERRED EMBODIMENTS

Figure 1:
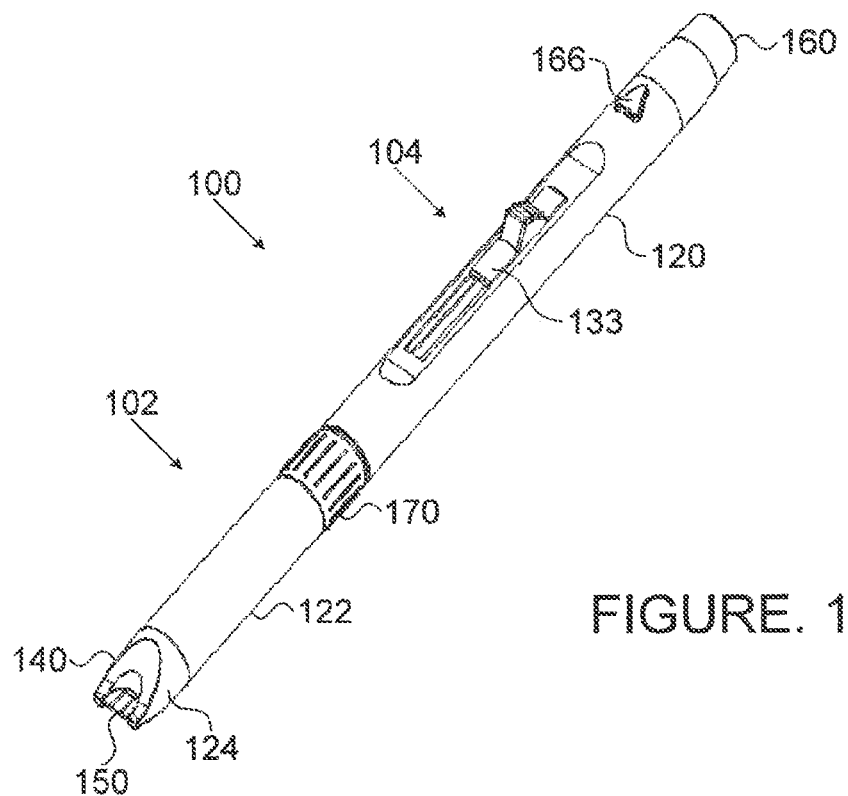
FIG. 1 is a schematic top view illustration of a physiological fluid testing apparatus (hereinafter: "PFTA") in accordance with variations of the present invention that is functionally adapted to perform blood tests.

In the following description, various aspects of a novel fully disposable apparatus adapted to allow performance of various fluids test such as toxicity tests in industrial pools and entertainment instruments such as swimming pool and to allow various physiological fluids test such as urine, blood, amniotic fluid, and saliva in an easy and friendly manner will be described. The novel disposable apparatus described herein is functionally connected to a smart phone installed with dedicated application software and relies on said smart phone at least for a power source and display means, and to transmit signals indicative of the measured parameter to said smart phone in a symbiotronic manner. The term "symbiotronic" as used herein is aimed to describe a symbiotic electrical relationship between the novel apparatus of the invention and a smart phone to form an all new device, such as a Glucometer. In order to allow, said symbiotronic relations and to perform various physiological fluid tests, dedicated application software is preinstalled on the smart phone that allows transformation of a measured level of a specific parameter in a physiological fluid sample obtained by a chemical reaction on a commercial strip, into a displayed number or other indicative symbol on the smart phone screen. Analysis of the data obtained from the commercial strip may be performed either on the disposable apparatus, or on the smart phone or on both, as will be described in details hereinafter. For the purpose of explanation, specific configurations and details are set forth in order to provide a thorough understanding of the apparatus.

Although various features of the disclosure may be described in the context of a single embodiment, the features may also be provided separately or in any suitable combination. Conversely, although the disclosure may be described herein in the context of separate embodiments for clarity, the disclosure may also be implemented in a single embodiment. Furthermore, it should be understood that the disclosure can be carried out or practiced in various ways, and that the disclosure can be implemented in embodiments other than the exemplary ones described herein below.

The descriptions, examples and materials presented in the description, as well as in the claims, should not be construed as limiting, but rather as illustrative.

Terms for indicating relative direction or location, such as "right" and "left", "up" and "down". "top" and "bottom", "horizontal" and "vertical", "higher" and "lower", and the like, may also be used, without limitation.

In accordance with embodiments of the present invention the novel apparatus provided herein may be used to perform various fluid test such as toxicity tests, and various biological tests produced from physiological fluids such as blood, urine, amniotic fluid, or saliva, such as glucose level, cholesterol level, coagulation test, pregnancy test (in blood or urine), HIV test, PH test, fetal lung maturation test, and more. The apparatus is preferably a small size fully disposable apparatus. It may be made of one unit or more. The apparatus is functionally connected to a smart phone and may rely on the phone for power supply, display means, storage and communication for operation. The electrical connection between the apparatus and the smart phone may be established by a connector from any kind known in the art and that is suitable for this purpose (Ear phone plug, USB, or other).

The apparatus provided herein is connected to a smart phone in a complementary manner, as the combination of the two together with specific software installed on the smart phone provides a novel system capable of performing various physiological fluids tests in a user friendly, fully disposable, and inexpensive manner. In addition, the apparatus may communicate besides of a cell phone or a Wi-Fi based phone, with any mobile device with a computing power such as an iPod or iPad, and it is may also communicate with any other tablet devices. Similarly, the novel apparatus provided herein may communicate with any computing devices such as a Laptop.

Wikipedia defines smart phone as the following: "A smart phone is a mobile phone that offers more advanced computing ability and connectivity than a contemporary basic feature phone. Smart phones and feature phones may be thought of as handheld computers integrated within a mobile telephone, but while most feature phones are able to run applications based on platforms such as Java ME, a smart phone usually allows the user to install and run more advanced applications. According to a study by ComScore, over 45.5 million people in the United States owned smart phones in 2010 and it is the fastest growing segment of the mobile phone market, which comprised 234 million subscribers in the United States. Thus, by using a smart phone as a platform for example for performing various fluid test in combination with the novel fully disposable apparatus of the present invention, as an hand held miniature mobile laboratory, it may provide mass of people worldwide an opportunity to easily monitor and follow up various physiological parameters including without limitation, glucose levels, cholesterol levels, hemoglobin level etc., without the need to go to the doctor and without the need to go to a laboratory in order to • performs such biological tests and to wait usually few days until they have the results. In addition, the proposed platform and the novel apparatus provided herein, allow many diabetic people worldwide, that should monitor their glucose level in a daily manner a simple, friendly, fully disposable, and minimally burdening platform to do this compared with currently available Glucometers (both, transplanted glucose monitoring systems and non transplanted systems). Furthermore, according to the international Diabetes federation (www.idf.org) much of the population in developing countries is not being followed properly in light of the costs and the logistics of the currently available devices and their analysis. The proposed platform together with the novel apparatus provided herein may solve this problem and provide a simple, non expensive and easy to perform solution.

In accordance with features of the invention, for testing a blood sample the apparatus may comprise the general following components: a lancing device to sample blood from a finger, forearm or palm of a user; an electrochemical strip, such as a glucose strip or a cholesterol strip adapted to collect blood sample and to produce data; and an electrical circuit that is functionally adapted to receive the data produced by said electrochemical strip and translate the chemical results into an electronic signal (analog or digital) that is, preferably, transmitted to a smart phone, either by wire or wireless transmission. Data transmission from the apparatus of the invention to a smart phone may be performed either by physical attachment of the two, for example by plugging the apparatus into the headset jack of the smart phone. Alternatively, it may be transmitted in a wireless mode in any form known in the art (e.g. Bluetooth, infra red, radio frequency, sound, RFID etc.).

For testing a urine sample, saliva sample or amniotic fluid sample the apparatus may comprise an electrochemical or chemical strip adapted to absorb the liquid sample and to produce data, and an electric circuit that is functionally adapted to receive the data produced by said electrochemical or chemical strip and translate the chemical results into an electronic signal (analog or digital) that is preferably, transmitted to a smart phone.

The electrochemical or chemical strip could be test-specific strips (for example glucose strip, cholesterol strip, pregnancy strip, protein strip, etc.)

In accordance with one feature of the present invention, a fluid testing apparatus for performing parameter measurement in a fluid sample is provided. The apparatus comprises: a strip adapted to absorb a fluid sample and to produce a signal indicative of said parameter level in said sample; and an adaptor adapted to connect said strip to a smart phone to thereby allow delivery of the produced signal or a correlated signal to said smart phone for obtaining a measurement of said fluid parameter displayed on said smart phone, wherein said testing apparatus relies on said smart phone at least for power supply and display means. The produced signal or a correlated signal may be processed at least partially by said fluid testing apparatus before delivery to said smart phone. Alternatively, the produced signal or a correlated signal may be delivered to said smart phone for processing by a dedicated application software installed on said smart phone. In accordance with one variation, processing may be conducted by reading the peak and timing of peak of a current of a voltage signal obtained upon loading the fluid sample on said strip. The adaptor may comprise an electrical circuit adapted to allow communication between said strip inner circuit and a connecting plug adapted to allow delivery of the produced signal or a correlated signal to said smart phone. The adaptor may further comprise a micro control unit and may be adapted to perform at least partial processing of said signal prior to delivery of said signal to said smart phone. Upon delivery of said signal or a correlated signal to the smart phone, processing of said signal is performed by dedicated application software installed on said smart phone, and a measurement is being displayed on said smart phone. In accordance with a further variation of the invention, the apparatus further relies on said smart phone for storage of data and communication. The measured parameter in accordance with variation of the invention may be a toxic substance.

In accordance with the present invention, the strip may be either one of a chemical strip or an electrochemical strip, and the signal transferred to the smart phone is either an electric current signal or a voltage signal.

The fluid sample may also be a physiological fluid, such as a blood sample, a urine sample, an amniotic fluid sample, and a saliva sample, or a mixture thereof. In such variation, the measured parameter may be for example, a glucose level, cholesterol level. HbA1C level, Hemoglobin level, fetal lung maturation level, and PSA level. In a specific variation of the invention, the apparatus is adapted to perform blood tests and comprises at least two separable subunits, first subunit comprises at least: a lancing device and housing; and second subunit comprises at least: a slot adapted to allow collection of said physiological fluid sample, a strip, an adaptor to thereby allow physical attachment and signals transmission between said testing apparatus and said smart phone, and housing. In such variation, the apparatus may further comprise a thread that functionally allows a user to adapt said lancet length to his physical dimensions.

The apparatus provided herein may functionally be connected to said smart phone either via the headset jack or via a USB entry to thereby obtain at least a power supply and display means from said smart phone. The signal indicative of said parameter level may be delivered to the smart phone either via the headphone jack or via a USB entry, or it may be transmitted wirelessly. The apparatus is preferably fully disposable. In accordance with one another variation the apparatus may be connected and rely on a tablet device (such as iPad) or an iPod instead of a smart phone.

The present invention further provides a physiological fluid testing apparatus for performing a parameter measurement in a fluid sample comprising: A strip adapted to absorb a physiological fluid sample and to produce a signal indicative of said parameter level in said sample: An adaptor adapted to connect said strip to a smart phone to thereby allow delivery of the produced signal or a correlated signal to said smart phone for obtaining a measurement of said fluid parameter displayed on said smart phone, wherein said physiological fluid testing apparatus relies on said smart phone at least for power supply and display means. The produced signal or a correlated signal may be processed at least partially by said testing apparatus before delivery to said smart phone. Alternatively, the produced signal or a correlated signal may be delivered to the smart phone for processing by dedicated application software installed on said smart phone. The fluid sample in such variation may be either one of a blood sample, a urine sample, an amniotic fluid sample, a saliva sample, or a mixture thereof, and wherein, said measured parameter is either one of a glucose level, cholesterol level, HbA1C level, Hemoglobin level, fetal lung maturation level, and PSA level. The apparatus is preferably fully disposable. In one another variation, it may be connected and rely on a tablet device (such as iPad) or an iPod instead of a smart phone.

In one further variation of the invention, a blood testing apparatus for performing glucose measurement in a blood sample is provided. The apparatus comprising: A glucose strip adapted to absorb a blood sample and to produce a signal indicative of the glucose level in said blood sample; and an adaptor adapted to connect said glucose strip to a smart phone to thereby allow delivery of the produced signal or a correlated signal to said smart phone for obtaining a measurement of the glucose level displayed on said smart phone, wherein said blood testing apparatus relies on said smart phone at least for a power supply and display means. In such variation, the produced signal or a correlated signal is being processed at least partially by said blood testing apparatus before delivery to said smart phone. Alternatively, the produced signal or a correlated signal is delivered to said smart phone for processing by a dedicated application software installed on said smart phone. Processing may be conducted by reading the peak and timing of peak of a current or a voltage signal obtained upon loading the blood sample on said glucose strip. In such variation, the apparatus is preferably fully disposable. In one another variation, the apparatus may be connected and rely on a tablet device (such as iPad) or an iPod instead of a smart phone.

The invention is further directed to a method for performing a fluid parameter measurement in a fluid sample comprising the steps of: Installing a dedicated application software on a smart phone; Loading a fluid sample on a fluid testing apparatus, said apparatus comprising: a strip adapted to absorb such sample and to produce a signal indicative of said parameter level in said sample; and an adaptor adapted to connect said strip to a smart phone to thereby allow delivery of the produced signal or a correlated signal to said smart phone for obtaining a measurement of said fluid parameter displayed on said smart phone, wherein said testing apparatus relies on said smart phone at least for a power supply and display means; Inserting said loaded fluid testing apparatus into a headset jack of a smart phone to thereby allow communication between said apparatus and said smart phone and delivery of power supply; and obtaining the measured parameter level displayed on said smart phone screen. The loaded fluid testing apparatus may be connected to said smart phone via a USB entry. The produced signal may be delivered to the smart phone either via the headset jack, via a USB entry, or it may be transmitted wirelessly. Alternatively, the apparatus may be connected and rely on a tablet device (such as iPad) or an iPod instead of a smart phone. In accordance with one specific variation, the tested fluid is a physiological fluid, such as blood, urine, an amniotic fluid, saliva, or a mixture thereof. The measured parameter may be for example, a glucose level, cholesterol level, HbA1C level, Hemoglobin level, fetal lung maturation level, and PSA level. The strip may be either one of a chemical strip or an electrochemical strip, and the signal transferred to the smart phone may be either an electric current signal or a voltage signal. The produced signal or correlated signal may be processed at least partially by said fluid testing apparatus before delivery to said smart phone. Alternatively, the produced signal or a correlated signal may be delivered to said smart phone for processing by a dedicated application software installed on said smart phone. In one specific variation, processing is conducted by reading the peak and timing of peak of a current of a voltage signal obtained upon loading the fluid sample on said strip.

The present invention further provides a method for performing glucose measurement in a blood sample comprising the steps of: Installing dedicated application software on a smart phone; Loading a blood sample on a glucose measurement apparatus, said apparatus comprising: a strip adapted to absorb blood sample and to produce a signal indicative of said glucose level in said sample; and an adaptor adapted to connect said strip to a smart phone to thereby allow delivery of the produced signal or a correlated signal to said smart phone for obtaining a measurement of said glucose level displayed on said smart phone, wherein said glucose measurement apparatus relies on said smart phone at least for a power supply and display means; Inserting said loaded glucose measuring apparatus into a headset jack of a smart phone to thereby allow communication between said apparatus and said smart phone and delivery of power supply; and obtaining the measured glucose level displayed on said smart phone screen. In such variation, the loaded glucose measurement apparatus may be, alternatively, connected to said smart phone via a USB entry. The signal produced may be delivered to said smart phone either via the headset jack, via a USB entry, or it is transmitted wirelessly. The apparatus is preferably fully disposable. In one another variation, the apparatus may be connected and rely on a tablet device (such as iPad) or an iPod instead of a smart phone.

The application is further directed to a blood glucose monitoring apparatus for determining glucose level in a blood sample of a user comprising: a lancing device adapted to allow said user obtaining a blood sample; a slot adapted to allow collection of said blood sample; a glucose strip adapted to absorb said blood sample and to produce a signal indicative of said glucose level in said sample; and an adaptor adapted to functionally connect said glucose strip to a smart phone via a connecting plug designed to be inserted into a headset jack of a smart phone to functionally deliver to said smart phone the produced signal or a correlated signal thereof, and to allow said apparatus obtain at least a power supply and display means from said smart phone.

The invention is also directed to a mobile hand held, miniature laboratory system capable of performing fluid parameter measurement of a sample, said system comprising: a smart phone installed with dedicated application software; a strip adapted to absorb a fluid sample and to produce a signal indicative of said parameter level in said sample; and an adaptor adapted to connect said strip to a smart phone to thereby allow delivery of the produced signal or a correlated signal to said smart phone for obtaining a measurement of said fluid parameter displayed on said smart phone, wherein said testing apparatus relies on said smart phone at least for a power supply and display means. In a specific variation the fluid sample may be a physiological fluid sample such as, a blood sample, a urine sample, an amniotic fluid sample, a saliva sample, or a mixture thereof, and wherein, said measured parameter is either one of a glucose level, cholesterol level, HbA1C level, Hemoglobin level, fetal lung maturation level, and PSA level.

Reference is now made to the figures.

Figure 2:
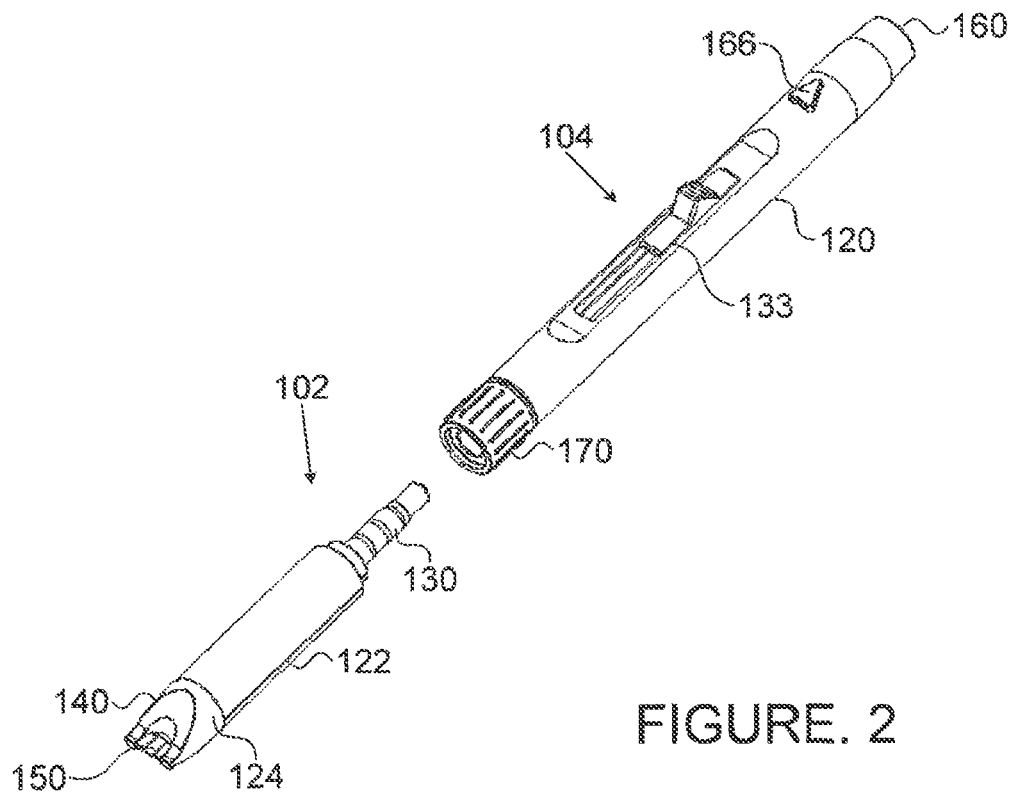
FIG. 2 is an upper front view illustration of PFTA 100 of FIG. 1 in a detached position.

FIG. 1 is a schematic top view illustration of a physiological fluid testing apparatus in accordance with variations of the present invention that is functionally adapted to perform blood tests. PFTA 100 illustrated in FIG. 1 is in a packed form and composed of two subunits 102 and 104. However; it is clear to a man skilled in the art that such apparatus could be composed of one subunit only, or alternatively it may be composed of more than two subunits according to a desired design. First subunit 102 comprises a housing 122, a slot 140 for collecting a blood sample located at the distal end of subunit 102 away from subunit 104 and a chemical strip 150. Slot 140 is preferably but not necessarily made of a transparent cover 124 that provides the user a convenient view for indicating whether the blood sample bas reached strip 150. First subunit further comprises an adaptor 180 that comprises an electrical circuit (not shown) attached to a PCB (printed circuit board), connecting socket to connect the chemical strip to the PCB, and a connecting plug 130 such as an audio jack output, that is functionally adapted to be inserted into an audio jack port of a smart phone, or other computerized device as mentioned above and functionally to transmit/deliver the signals obtained from the strip or correlated signals to the smart phone. Connecting plug 130 may be connected to a plain electric circuit that is aim to allow communication between connecting plug 130 and strip 150 (and to deliver a non processed signal), or it may be connected to a complex electric circuit with a Micro control unit (MCU) that fully or partially analyzes the signal produced by the strip (and to deliver a processed signal). The other end of connecting plug 130 that is free is adapted to be inserted into the headset jack of a smart phone to physically connect subunit 102 to said smart phone (not shown in this figure). Second subunit 104 generally comprises a housing 120, a cocking mechanism 133 that is adapted to cock a lancet upon usage, a lancet trigger 166, and a lancet opening. The term "lancet" as used herein also refers to a needle. When subunit 102 is connected to subunit 104 cocking mechanism 133 is unable to function, wherein the connection between the two subunits functionally serves as a safety mechanism. Subunit 104 may also comprise a thread 170 that may cover the connection area of subunit 102 and subunit 104 and allows a user to set the lancet length to be protruded upon pressing the lancet trigger 166. This mechanism allows a user to adapt it to its physical dimensions. The attachment of subunit 102 and 104 may be based on structural fitting of the attached components as shown in FIG. 2. A detailed description of the functionality of the components mentioned in the above will be made with reference to FIG. 4 hereinafter. Although the general structure of PFTA 100 is the same, minor changes may be made in accordance with the type of fluid tested (urine, blood, saliva, amniotic fluid, or other), and accordingly the chemical strip comprised in the specific apparatus should be suitable for the parameter measured. The packed form of PFTA 100 and variation thereof may be available to a user as OTC merchandise in a pharmacy or supermarket according to local regulation, or sold via other means, such as over the internet, or as an add-on to health products, such a diet meals plans.

FIG. 2 is an upper front view illustration of PFTA 100 of FIG. 1 in a detached position. In this figure first subunit 102 and second subunit 104 are detached from each other, ready to be used. In such position, in addition to the components viewed in FIG. 1, connecting plug 130 is exposed.

Figure 3:
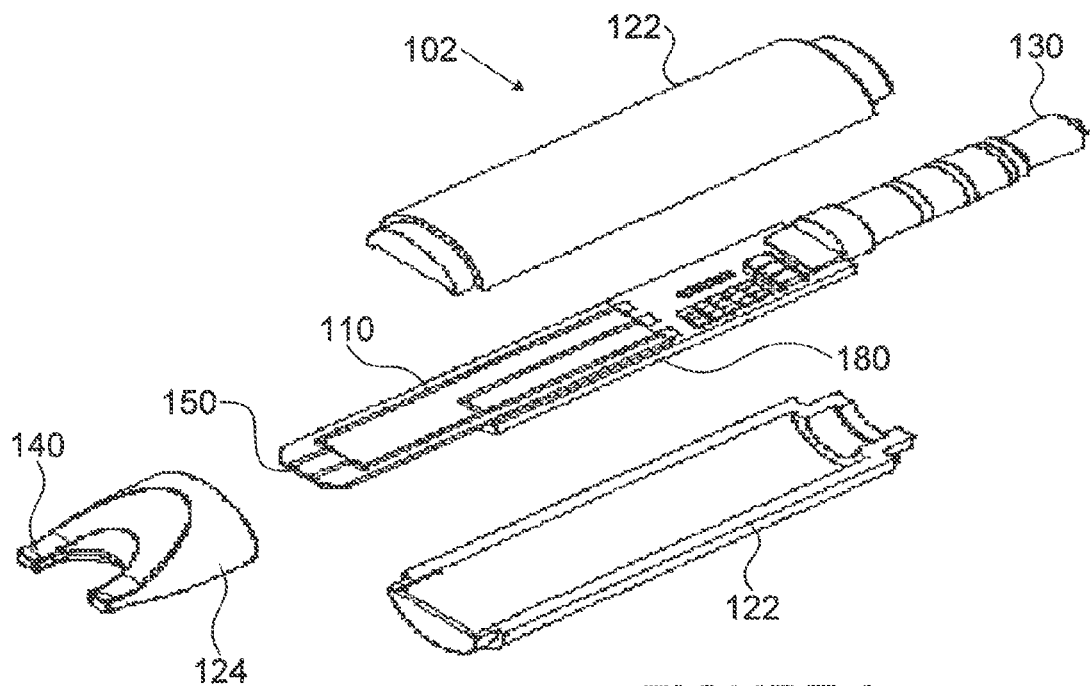
FIG. 3 is a schematic "bomb view" illustration of subunit 102 of PFTA 100 of FIG. 1 showing all the components comprised in subunit 102 in accordance with variations of the invention

FIG. 3 is a schematic "bomb view" illustration of subunit 102 of PFTA 100 of FIG. 1 showing all the components comprised in subunit 102 in accordance with one variation of the invention. Shown in this view are: housing 122 (upper and lower parts), slot 140 within transparent cover 124, chemical strip 150, adaptor 180 comprising connecting plug 130 and electric circuit 110. As shown in this figure connecting plug 130 is adapted to be inserted into an audio jack port of a smart phone (such as an iphone, or android) device and comprises three rings (left, right and microphone). Detailed description of adaptor 180 including plug 130 and audio jack pins 510 will be described in details with reference to FIGS. 5-6 hereinafter.

Figure 4A:
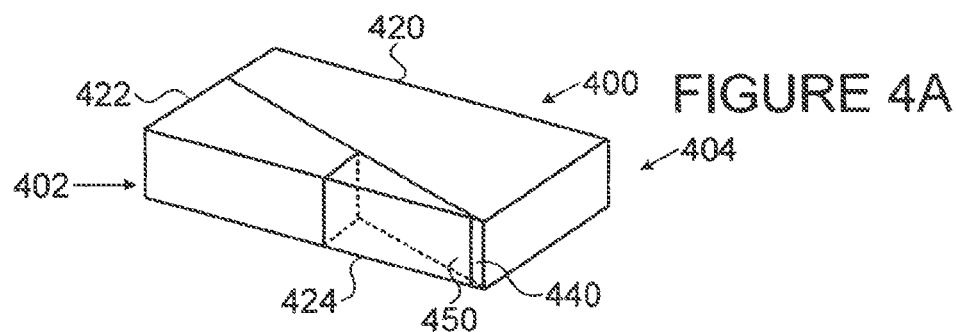
FIGS. 4A-C are schematic illustrations of another variation of physiological fluid testing apparatus in accordance with the present invention that is functionally adapted to perform blood tests.
Figure 4B:
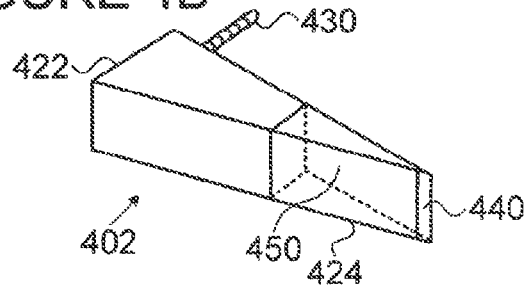
Figure 4C:
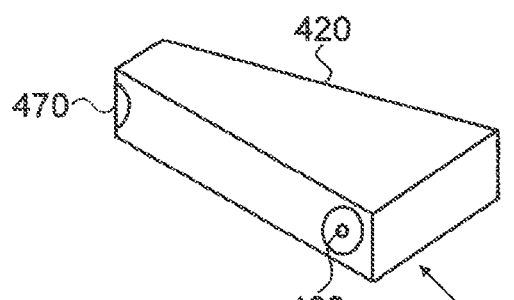

FIGS. 4A-C are schematic illustrations of one another variation of physiological fluid testing apparatus in accordance with the present invention that is functionally adapted to perform blood tests. FIG. 4A is an upper front view illustration of PFTA 400 in a packed form made of two subunits; FIG. 4B is an upper front view of first subunit 402 of PFTA 400; FIG. 4C is an upper front view of second subunit 404 of PFTA 400.

In more details, FIG. 4A illustrates one another variation of PFTA in accordance with the present invention in a packed form.

FIG. 4B is a schematic illustration of subunit 402 of PFTA 400. This subunit, is physically attached via connecting plug 430 of adaptor 180 to a smart phone device at least for receiving its power source and display means, and serves for the collection of a drop of blood, through slot 440, into a dedicated strip 450 (for example glucose or cholesterol strip), covered with a transparent cover 424, where it is connected to specially designed electric circuit (not shown) hidden in the subunit's housing 422, where the electrochemical analysis of parameter level in a fluid sample (for example blood glucose level, or cholesterol level) is processed and transmitted to the smart phone. In accordance with one another variation of the invention. PFTA 400 comprises a basic electric circuit that only allows transmitting/delivering the signals measured by the electric circuit of the chemical strip 150 to the smart phone for processing and analysis. The two different operating modes and optional measurement circuits for each of them is described in details with reference to FIGS. 5-13. Transmission to the smart phone (or to other computerized device such as iPad or iPod), may be carried out either by connecting plug 430 (Earphone or USB plug), or wirelessly, for further data collection, displaying, storage in memory, communication, and further usage. The electrical circuit hidden in housing 422 may send to the smart phone digital or analog signals, where these signals will be translated (if necessary) to digital information, that will be displayed on the smart phone screen as fluid chemical's concentration value (for example blood glucose level, hemoglobin level, PSA level, cholesterol level, etc.).

The transparency character of cover 424 allows the user to visualize the absorbance, by capillary forces, of an adequate amount of blood sample by the electrochemical glucose strip 450. The ability to visualize the absorbance of the sample by strip 450 is convenient for the user and allows him/her monitoring that a proper amount of blood sample has reached the proper location to thereby perform the required test adequately.

In a packed form (FIG. 4A), plug 430 may serve also for establishing a physical connection with subunit 404 (FIG. 4C) through socket 470 located in subunit 404 (FIG. 4C). The connection between the two subunits in accordance with this variation of the invention is mechanical attachment that is based on complementary structure of the components involved. In the unpacked pre-operative form, plug 430 is released from socket 470 ready to be inserted into a smart phone via a suitable socket (headphone jack or a JUSB entrance). The physical and functional connection between subunit 402 and a smart phone, through connecting plug 430, is a "Symbiotronic" connection, meaning, that the physical connection of the two electronic platforms, the smart phone and subunit 402, produces a new device such as a Glucometer.

While the smart phone brings power source, display means, control buttons (either virtual or non virtual), memory for storage, and communication abilities (either by cellular connection or by web connection) and adequate operation software, while subunit 402 brings the ability to collect fluid sample and the production of a processed electrical signal, which is understood by a said specific application software pre installed on the smart phone, allowing the processing and display of a specific chemical's concentration value that is being tested in a physiologic fluid sample. The reliance on the smart phone for power supply, processing, communication, storage, and display, enables potentially significant simplification of the glucose meter, a fully disposability of the apparatus, and a meaningful reduction of its costs.

The physical connection is preferably to an analog outlet of the smart phone but it may also be established to a digital outlet. In such a scenario, a digital to analog converter is required as part of the electrical circuit comprised in housing 422. The transmission of data from subunit 402 to the smart phone may also be conducted via connecting plug 430. Additionally or alternatively transmission of data may be conducted via other physical connection between subunit 402 and the smart phone or it may be conducted in a wireless manner by any wireless connection known in the art including without limitation Bluetooth, Radio Frequency (RF), Infra Red (IR), sound, and RFID. In such a scenario, subunit 402 will include the proper transmission components according to the transmission method selected. In a scenario that PFTA 400 comprises a specific electrical circuit with a micro processing unit that delivers the smart phone a processed signal correlative to a measured value in the fluid sample, only upon receipt of the processed signals the smart phone is capable of translating the data obtained, displaying it on a screen, keeping it in the smart phone's memory, compare it to former results, alert the user when the results are out of normal range, connect to an emergency center or to a family member when a life threatening situation is recognized (such as Hypoglycemia), or any other predetermined operation it is designed to perform. Thus, the combination of each variation of PFTA of the present invention and a smart phone provides a novel platform that is adapted to serve as a mobile, easy to use, fast operating, inexpensive, disposable, and ready to be used any time and anywhere (24/7) laboratory, capable of performing various physiological fluids specific tests. In the specific embodiment illustrated in FIG. 4, the combination of PFTA 400 with a smart phone may function as a user-friendly Glucometer capable of measuring glucose levels in the blood of any person, either a diabetic or non diabetic (e.g. for high risk for diabetes) person, in an inexpensive, easy to perform manner, releasing a person from the trouble of purchasing and carrying along a specific kit or the need for a special expensive time consuming visit to a medical doctor to be referred for a laboratory test.

FIG. 4C is a schematic illustration of subunit 404 of device 400 in an unpacked form, ready to be used. Subunit 404 in its unpacked form, in the case of a blood test, serves as a personal, disposable, unit for the test lancing device to prick one's skin (finger, arm, palm) allowing for the drawing of a tiny drop of blood to be tested by subunit 402 while connected symbiotronically to a smart phone. Subunit 404 comprises a housing 420, a complementary socket 470 that is functionally adapted to hook plug 430 in the packed form (FIG. 4A), a lancet opening 460, where it is attached to the skin of a person for pricking the skin, a releasing button (not shown) for firing the lancet, and another button (not shown) to cock the lancet device in the case that more attempts are needed.

In its packed form, subunit 404, which is firmly but reversibly, attached to subunit 402, serves as a cover for subunit 402, for protecting the test strip 450 from moisture, dust and any possible damage of any kind, and covering connecting plug 430 for the same purposes.

In the case of Urine, Amniotic fluid or Saliva tests, subunit 404 serves merely as a cover, for protection purposes, as mentioned above.

A user, intending to perform blood glucose test, separates the two subunits 402 and 404 thereof. Then, a user should attach subunit 402 to his smart phone that was pre-installed with specific application software as mentioned above. In accordance with one variation of the invention, while connecting the two pieces together the glucometer application pops up showing that the system is ready for glucose test. Next, a user uses subunit 404 to prick the skin for blood drawing and attaches the drop of blood to slot 440 of subunit 402 allowing for blood to be suctioned by capillary force into the test strip. After few seconds, test result appears on the smart phone screen. The glucometer application software installed of the smart phone allows the test results to be stored in the smart phone memory and allows displaying trends and history of previous glucose tests, for the evaluation of disease management and data transfer.

Figure 5A:
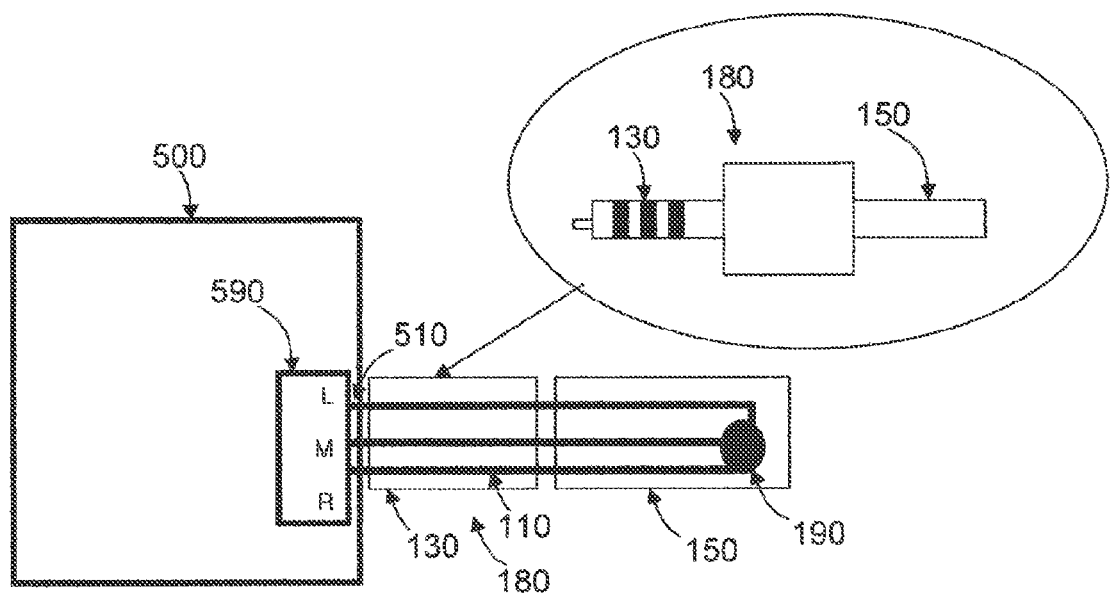
FIGS. 5A-C are schematic illustrations of an optional operation mode of PFTA 100 or PFTA 400 adapted to measure glucose level in the blood, in accordance with variations of the present invention (FIG. 5A), and two optional measurement circuits that may be used in such operation mode: A proposed measurement circuit with long recording time (FIG. 5B); and, a proposed measurement circuit with short recording time (FIG. 5C).
Figure 5B:
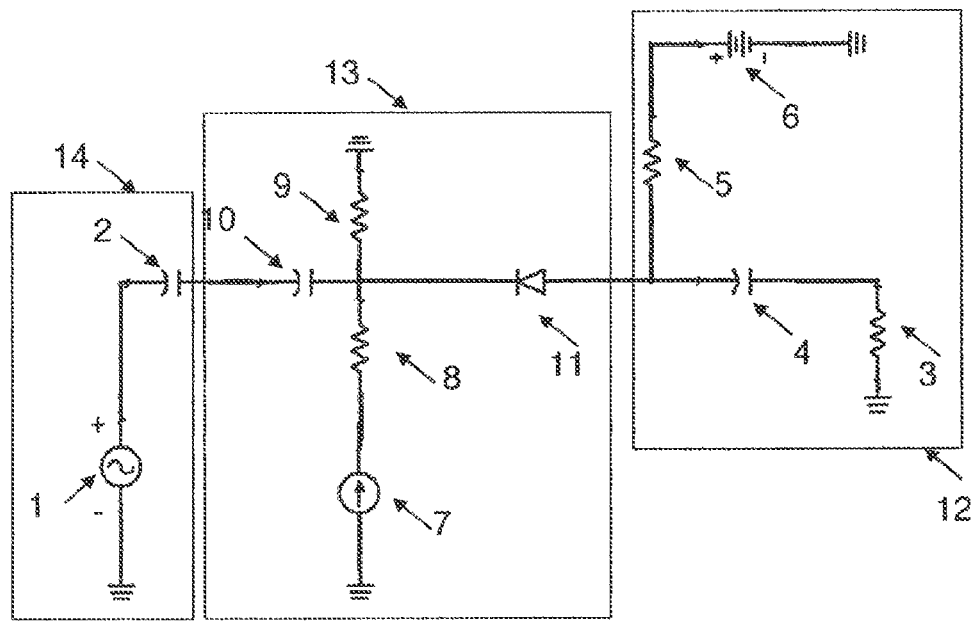
Figure 5C:
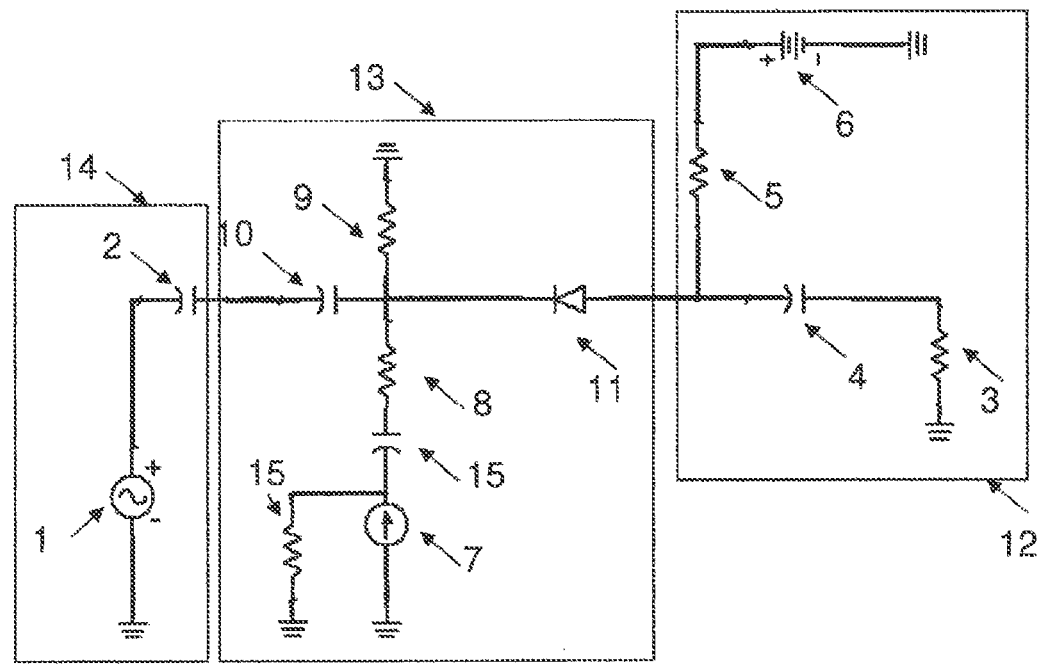

Reference is now made to FIGS. 5A-C that schematically illustrates an optional operation mode of PFTA 100 illustrated in FIG. 1 in accordance with variations of the present invention, and two optional electric circuits that may be used in such operation mode, wherein the apparatus in this example is adapted to measure glucose level in the blood. Shown in figure 5A: measurement unit 500, i.e. a smart phone that includes an audio jack port 590 for a microphone input M, and L and R speaker outputs, all denoted hereinafter as audio pins 510; Adapter 180 may comprise connecting means (not shown) to functionally connect glucose strip 150 to a PCB comprising an electric circuit 110; and a connecting plug 130 adapted to be attached to the PCB on one end and to be inserted into a headset jack of a smart phone on the other end to functionally deliver to the smart phone the produced signal or a correlated signal, either processed or non processed signal (according to the electric circuit in use) to thereby obtain and display a measurement of the physiological fluid parameter on the smart phone screen. Connecting plug 130 should match the smart phone's port. The electric circuit 110 may be a minimal electric circuit that may include several resistors, capacitors, diodes and inductors. Alternatively, it may comprise a MCU and additional electric components.

Test strip 150, which may be a commercial glucose strip, is being inserted to the appropriate header in this unit; also shown in this figure is blood sample 190.

Generally, Smart phone 500 generates a sinus wave either in a single frequency mode or a sweep mode, and outputs this sinus wave through an electric circuit 180 to the strip. Going through the blood sample, the waveform is modulated by the electrical properties of the blood and is being reread at the microphone input.

FIG. 5B illustrates an optional measurement electrical circuit (13) connected to the speaker output (14) and to the microphone input (12). Circuits (14) and (12) are general knowledge and make the fundamental (may appear with minor changes between several commercial products) circuit for a speaker output and microphone input. The speaker output is generally isolated by a series capacitor with a few μF of value.

Microphone input is composed of two main branches—ac input and dc output. In order to operate correctly, most of the microphones require a DC voltage that is generated by a DC power supply (6) at the microphone input. This DC voltage (6) is passed through a series resistor (5) generally 2.2 KOhm. In order for the internal A/D sampler not to be saturated by this DC voltage, the actual microphone input is isolated by a series capacitor (4) up to the trans-conductance amplifier's input impedance (3).

A glucose strip includes a chemical enzyme that reacts chemically with the glucose located in the blood. The chemical reaction generates current that flows in. This current passes through resistors (8) and (9) and is converted to a voltage drop.

Diode (11) is used as a toggle switch that in the above circuit is normally closed. That means that the microphone's internal DC voltage source (6) is forward biasing the diode while the current source is off (no measurement is taken). In such a scenario, the speaker output sinus wave is recorded by the microphone with minimal attenuation by the diode. When a glucose strip is inserted and blood is to be measured, the current generates a rise in the diode's cathode voltage and causes it to be higher than the anode voltage. This causes the diode to serve as an open circuit. When this occurs, the microphone records only noise, until the strip's current is low again and the diode returns to conduct. The time duration in which the sinus wave was shut down and no signal was recorded, is relative to the strip's glucose level. As the glucose level is higher, the time the diode is off is longer.

FIG. 5C illustrates alternative electrical circuit in accordance with variations of the present invention in which, recording time is shortened related to the measurement circuit of FIG. 5B. The measurement circuit illustrated in FIG. 5C generally functions in the same manner as the former circuit, except series capacitor (15) and parallel resistor (15). The parallel resistor (15) is used to convert the strip's current source into a voltage source. Additionally, capacitor (15), together with resistors (8) and (9) functions as a differentiator. This differentiator is functionally used to sense when the voltage generated by the current source reaches its peak. When this happens, a negative voltage is generated on resistor (9) and the diode returns to conduct. This operation shortens extensively the measurement period of time, thus enables a faster display of the measured parameter level.

Figure 6:
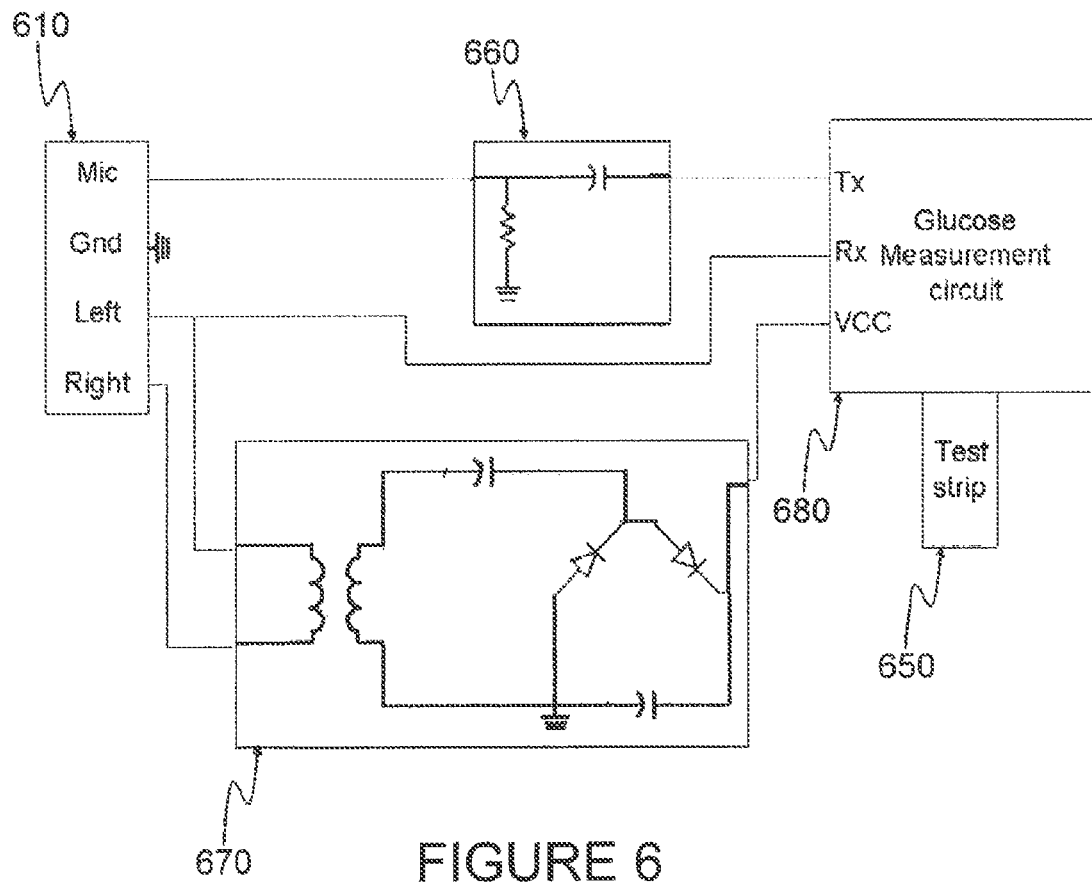
FIG. 6 is a schematic illustration of another optional measurement circuit of PFTA 100 or PFTA 400 adapted to measure glucose level in the blood in accordance with variations of the present invention.

Reference is now made to FIG. 6 that schematically illustrates one another measurement circuit in accordance with variation of the invention for measuring glucose level in a blood sample.

Smart phone's header connector usually comprises a microphone (mic) input and a Left and Right speaker outputs, all together denoted as "audio pins" 510. The mic input pin may be connected to a sensing circuit 660 that usually includes a parallel resistor and a series capacitor. Sensing circuit 660 is required to thereby allow the smart phone to "sense" whether an external mic circuit is connected. In accordance with one feature of the present invention, the mic input is fed by the physiological fluid parameter measured, e.g. with a glucose measurement unit Tx output obtained from glucose measurement circuit 680.

In order to allow the smart phone device to read the measurement obtained from the measurement module, a Tx pin is used as a platform for a frequency modulated signal. Once the measurement device is on, it generates an FSK signal (two distinct frequencies symbolize '0' and '1'), and through this signal, information regarding the status of the apparatus is transferred to the smart phone by transferring predetermined binary "words"; wherein each "word" represents a specific status. Additionally, the measurement module 680 may comprise a Micro processing Unit (MCU) that functionally allows the apparatus of the present invention to receive commands from the smart phone via the output pin (which in fact is a speaker output pin).

In order to operate correctly, the measurement module 680 requires a DC voltage. It receives its power via an AC/DC converter circuit 670, which include a transformer and a rectifier circuit. The smart phone generates a low voltage, high frequency sinus wave that is uploaded to higher voltages via the transformer. The high voltage sinus wave is rectified by a series capacitor and a diode. The output of this circuit is a steady DC voltage.

In more details, glucose measurement module 680 is functionally connected to test strip 650, and may be implemented by using MCU or analog circuit that converts currents/voltages to readable data. Such unit is able to communicate with the smart phone device, for example by FSK (Frequency Shift Keying) modulation commands. Smart phone device may additionally transmit FSK commands via one of its speaker outputs to glucose measurement circuit 680 via Rx input and the measured data and the apparatus status may be retransmitted to the smart phone via Tx output of FSK waveform. The FSK received signals are then analyzed by the smart phone and converted to real glucose measurements. In addition to the glucose measurement circuit described in the above, microphone (Mic) sensing circuit 610 is illustrated. This circuit functionally allows the smart phone device to sense when an external loading circuit is communicating with it via its microphone input and speaker outputs. Without this circuit, the smart phone device is not capable of recording data from the audio jack port.

Voltage rectifier circuit 670 receives from the speakers or earplugs output of the smart phone device sinus waves at specific and constant frequency. These sinus waves serve as an energy source that operates the electrical circuit. The sinus waves may be extracted from a single speaker output or from both as a balanced signal. The low voltage signals are up-converted to higher voltage levels and rectified with voltage doublers/rectifiers circuits 670. This rectifier circuit may contain diodes and capacitors with appropriate values.

Figure 7:
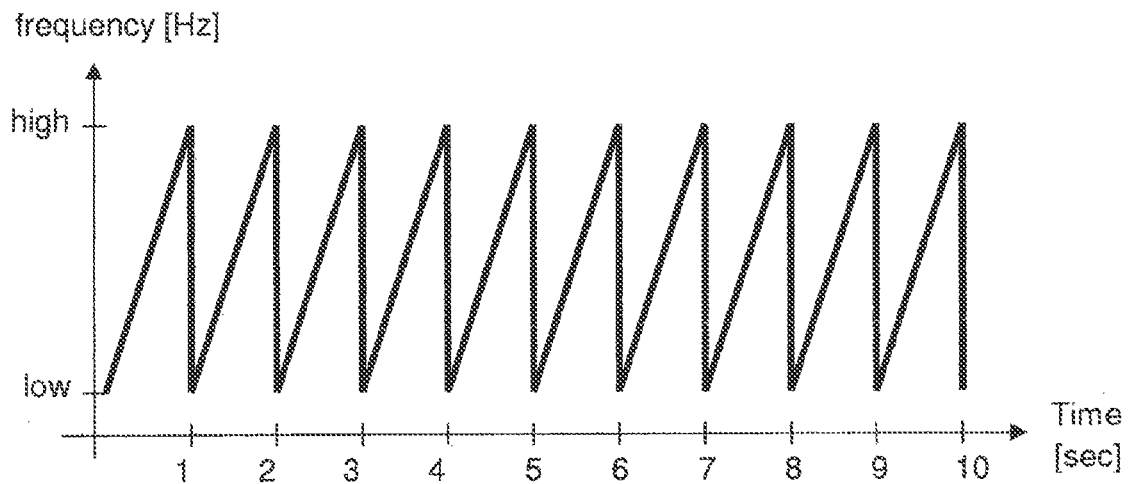
FIG. 7 is a schematic is a schematic illustration of a basic Chrip signal that smart phone generates in order to make glucose analysis from a chemical strip in accordance with variations of the present invention.

FIG. 7 is a graphic diagram of a chrip signal in accordance with one operational option of PFTA 100 of the present invention. A chrip signal is a basic waveform that the smart phone generates in order to conduct the glucose analysis of the strip. The smart phone outputs a chirp signal which is basically a sinus wave that is being swept by its frequency at a predefined rate. This sweep can be continuous or in a stepped regime. At each frequency point, the smart phone reads the microphone input signal and stores it. Once all the frequency points are measured, the smart phone processes the data and shows the result.

The next paragraph describes another measurement technique that is different from the one proposed previously. The above measurement unit measures the time delay the high frequency signal when recorded is off. For each delay there should be a distinct glucose value. The measurement technique illustrated herein is base on the idea that the strip's impedance (resistance of an object to high frequency signal) varies with glucose levels. For this, the speaker should output a sinus waveform in a single or swept frequency, passing through the sample and being modulated by it. The signal is than recorded by the microphone input circuit and analyzed in the smart phone. It should be emphasized that this is a novel measurement technique for measuring impedance in different frequency values.

In more details, before the blood sample is placed onto the test strip, the smartphone device sends a chirp signal through the test strip for calibration purposes. Then, after the sample is placed, smart phone device constantly sends chirp waves that measure the medium transmission function (which includes impedance). After several successive chirp measurements, the smart phone device is post processing the data and calculates the glucose levels of the sample. This technique for glucose measurement is based on measuring impedance of the test strip during its chemical reaction phase, and may be performed mutatis mutandis to other physiological fluid parameters being evaluated. In such measuring model, the smart phone device basically serves as an impedance analyzer in the frequency range of its speaker's amplifiers (100-20000 Hz).

More particularly, upon inserting subunit 102 (that comprises test strip 150 with a blood sample), smart phone device 500 transmits through its speaker output an electrical waveform that changes its frequency constantly. This waveform is known as a chrip signal. Smart phone 500 sweeps the whole frequency band in small time periods (less than 0.5 sec) and repeat the measurement for a few seconds. This is performed in order to monitor changes in the measurements that are solely related to the chemical reaction of the glucose measurement enzyme. With the measured data, the impedance of the blood sample is calculated and in a post measurement process, it is further converted to glucose levels.

Figure 8:
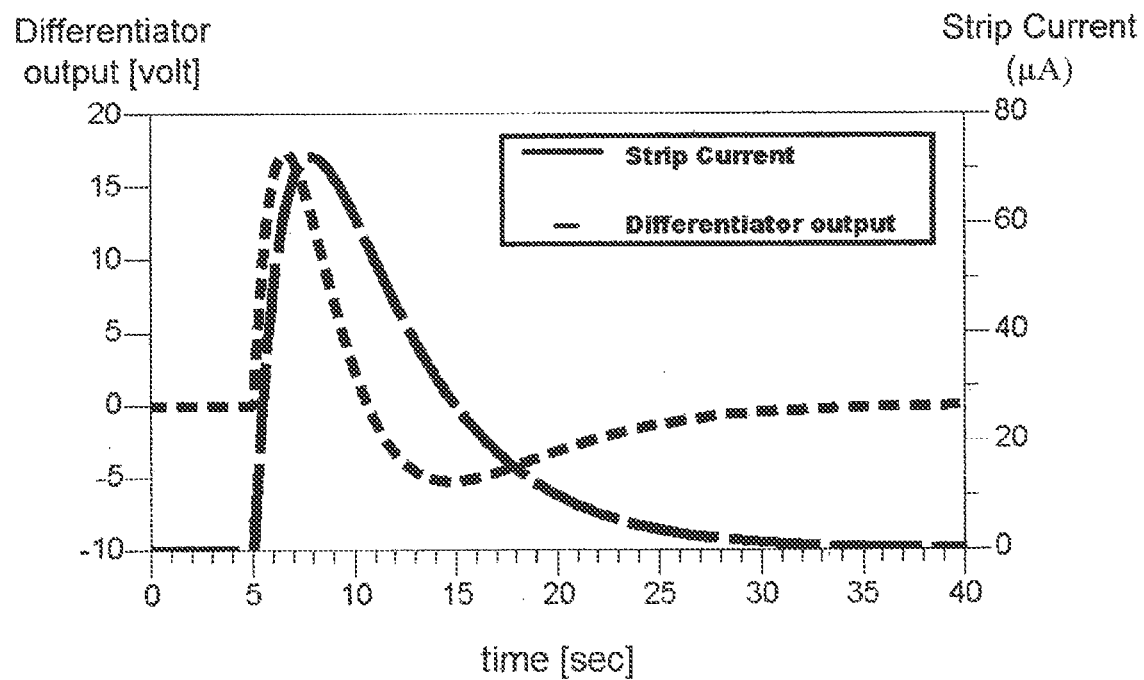
FIG. 8 is a graphic illustration of differentiator output voltage vs. strip current, in accordance with variations of the present invention.

FIG. 8 is a graphic presentation of differentiator output voltage vs. strip current of the electrical circuit of FIG. 5C that allows a short recording time. As shown in the figure, upon shortening of the recording time, the sinus waveform is lost for a shorter time period similarly to waveform of the long time recording circuit illustrated in FIG. 5B. However, though the rise time remains almost as before, the fall time of the current is being reduced dramatically (5 sec instead of 8 sec).

Figure 9A:
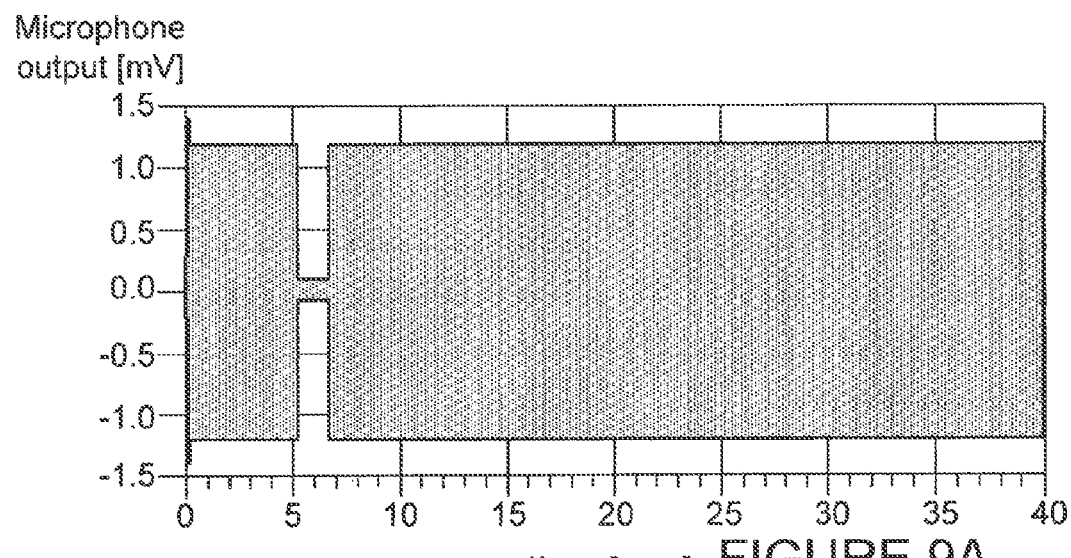
FIGS. 9A-C are graphic illustrations of 100 Hz speaker signal vs. glucose level of 48 mg/dL (9A); 198 mg/dL (9B); and 393 mg/dL (9C) in accordance with the present invention as described in FIG. 5C.
Figure 9B:
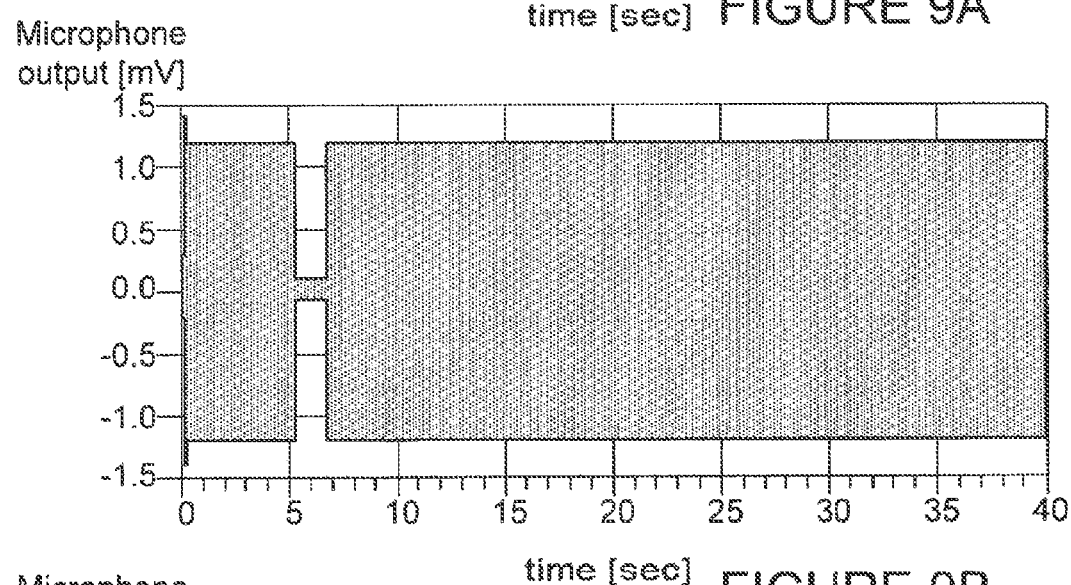
Figure 9C:
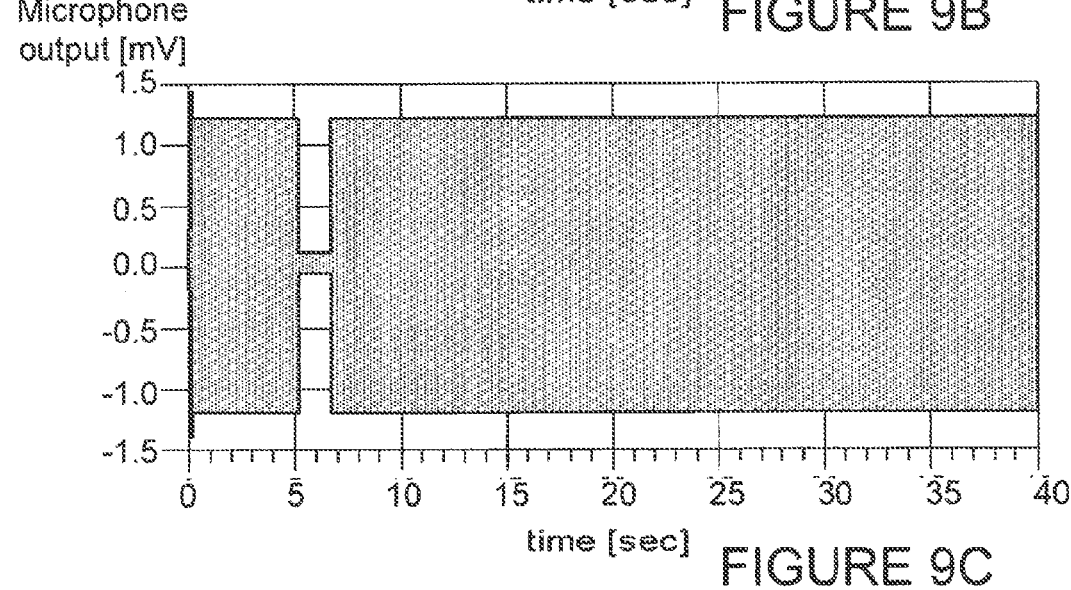

FIGS. 9A-C are graphic illustrations of 100 Hz speaker signal vs. glucose level of 48 mg/dL (9A); 198 mg/dL (9B); and 393 mg/dL (9C) in accordance with variations of the invention. As shown in the figure the glucose value is related to the time the pulse is off. As the glucose level in the blood sample rises the time period the pulse is off is extended.

Figure 10:
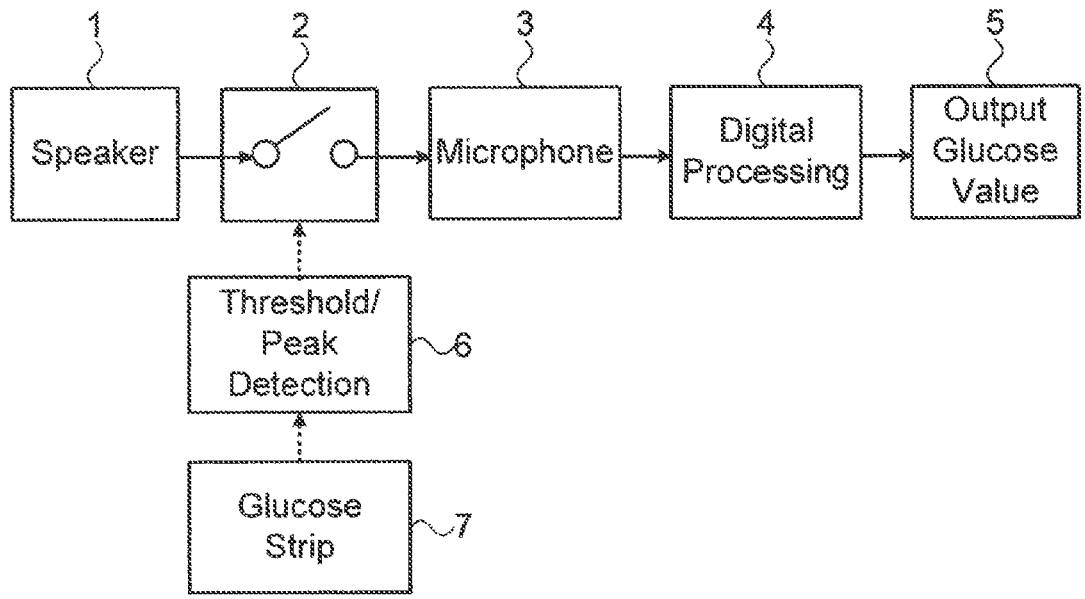
FIG. 10 is a schematic functional block diagram of the PFTA 100 of FIG. 1, and a smart phone in accordance with variation of the invention.

FIG. 10 is a schematic functional block diagram of the PFTA shown in FIG. 1, and a smart phone in accordance with variation of the invention. It is well known in the art that in order to measure glucose levels it is possible to measure either the peak current of the pulse (as most gluco-meter does) or the Time Of Appearance (TOA) of the peak. This TOA is measured as the time that the pulse current (or voltage) is above a pre-defined threshold. As glucose levels are higher, the TOA gets longer. Thus by measuring this TOA, it is possible to link this parameter to the actual glucose levels.

As illustrated in the figure, Speaker (1) generates a sinus wave with a specific frequency and amplitude. The waveform is passed through a normally close switch (2) in order to be recorded by the smart phone's microphone (3). When a glucose measurement begins, prior to the insertion of blood sample to the measurement strip (7), the speaker's output signal is continuously recorded. When the blood sample is loaded, circuit (6) monitors the strip's voltage/current. When it passes a certain threshold, it toggles the switch to OFF mode and the smart phone records only noise. In accordance with one variation of the invention, this mode will continue until the strip's current/voltage will drop below the threshold. In accordance with one another variation of the invention, this mode will continue until the strip's current/voltage will start to drop (peak detection). It is clear to a man skilled in the art that switch (2) may be set to a normally opened working mode and upon crossing the threshold value circuit (6) toggles the switch to ON mode.

Once recording the measurement is completed, software (4) starts processing the recorded measurements and analyze the time period where the signal was OFF/ON. This period is relative to the glucose level. When a result is reached, its value is plotted onto the system GUI, displayed and may be further stored in a data base.

Figure 11:
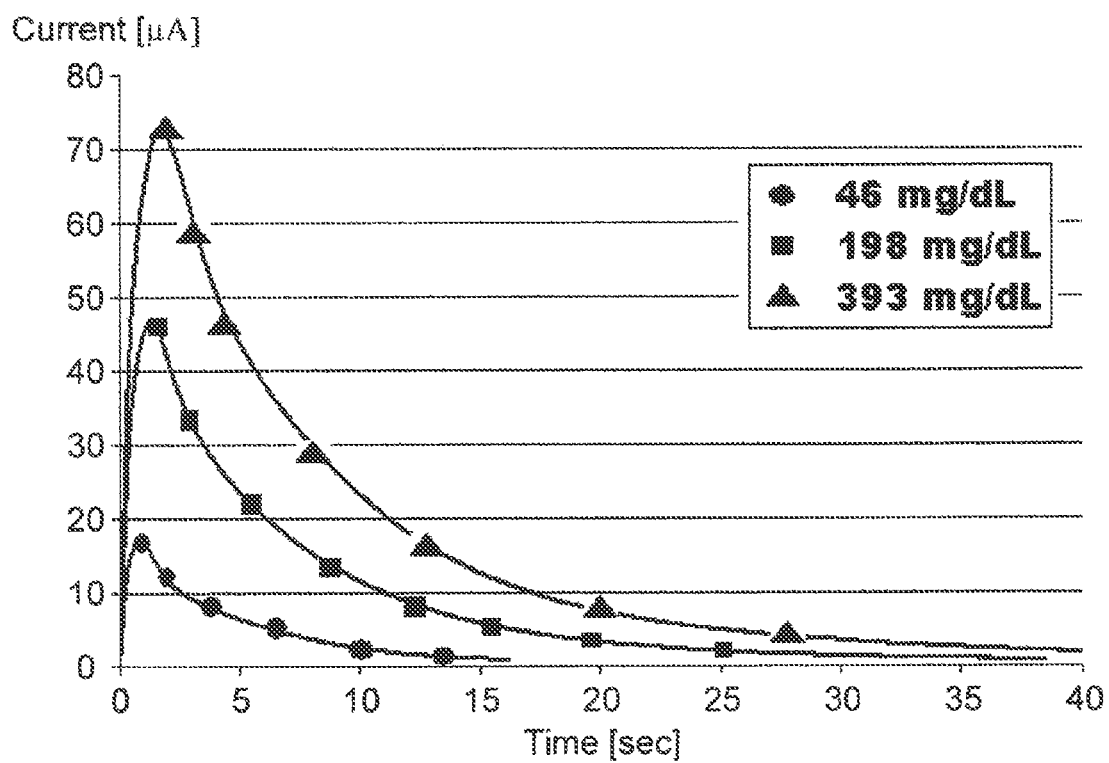
FIG. 11 is a graphic illustration of typical current values generated by a glucose strip following a chemical or an electrochemical reaction.

FIG. 11 is a graphic illustration of typical current values generated by a glucose strip following a chemical reaction. As illustrated in the figure, typical current values are generated by a standard glucose strip. The current generated has an exponential charging/de-charging nature with maximal peak and time constant relative to the glucose level. When the glucose level is higher, the current is also higher and the periods of charging and de-charging are elongated respectively.

Figure 12:
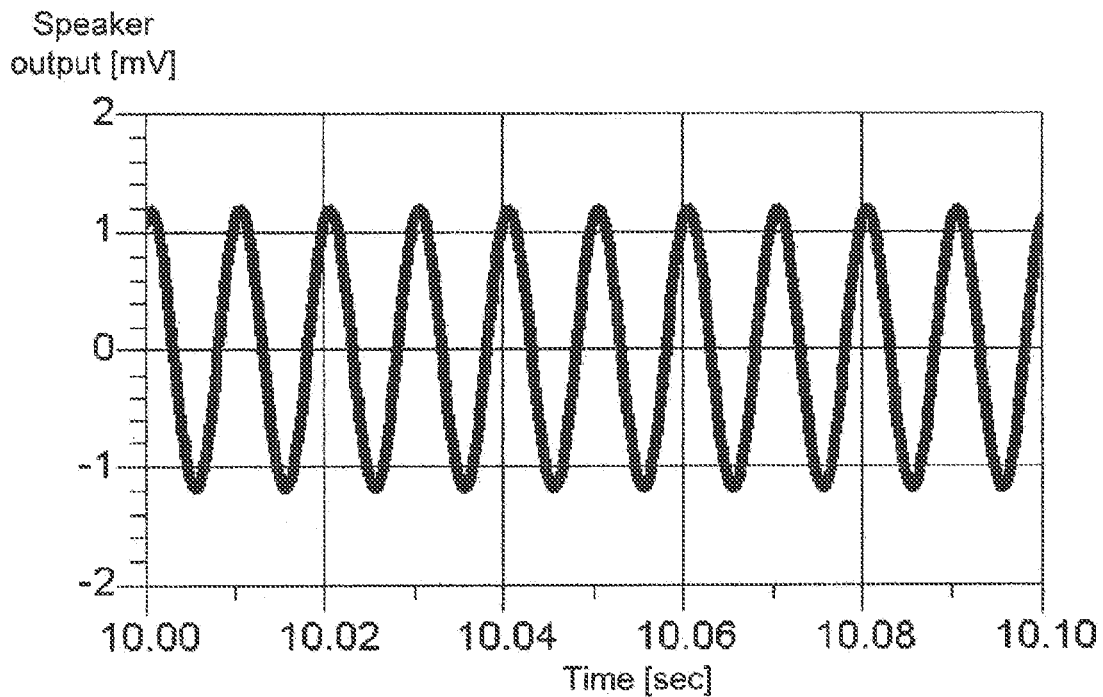
FIG. 12 is a graphic illustration of typical sinus wave generated by a speaker of a smart phone for it to be recorded by the smart's phone microphone as a baseline waveform.

FIG. 12 is a graphic illustration of typical sinus wave generated by a speaker of a smart phone for it to be recorded by the smart phone's microphone. As shown in the figure, a typical sinus wave is generated by the speaker for it to be recorded by the smart phone's microphone. The frequency, amplitude and shape of the waveform may be sinus wave or any other waveform. When an external device is connected to the smart phone, additional wave is mounted on this inner recorded wave. A graphic illustration of such scenario is illustrated in FIGS. 13A-13C.

Figure 13A:
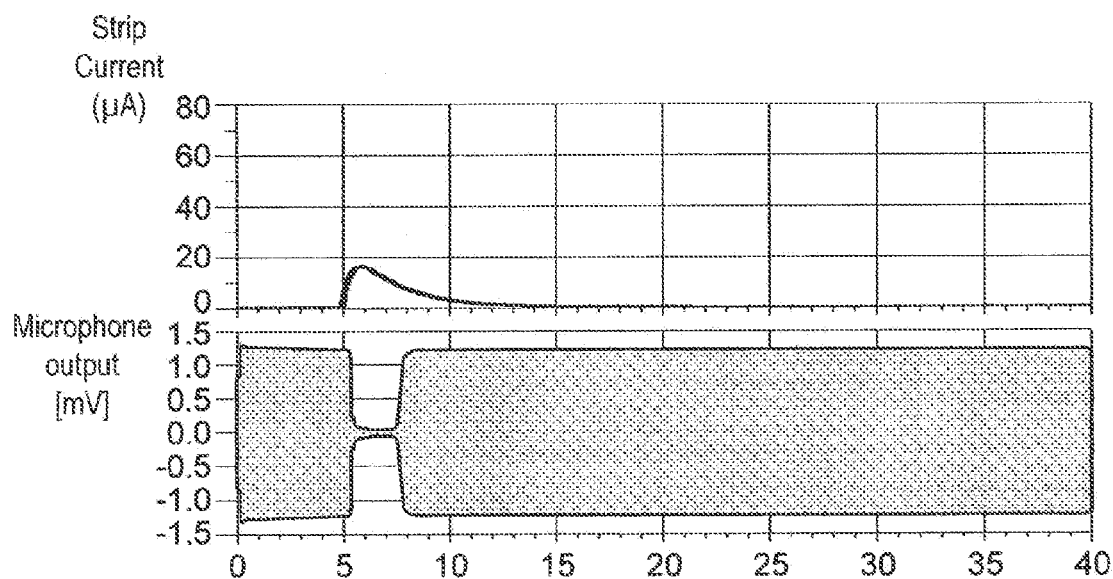
FIGS. 13A-C are graphic illustrations of a strip current (top part) and a microphone recorded waveform (bottom part) for three distinct glucose values 48 mg/dL (13A), 189 mg/dL (13B), and 393 mg/dL (13C) in accordance with variations of the invention as described in FIG. 5B.
Figure 13B:
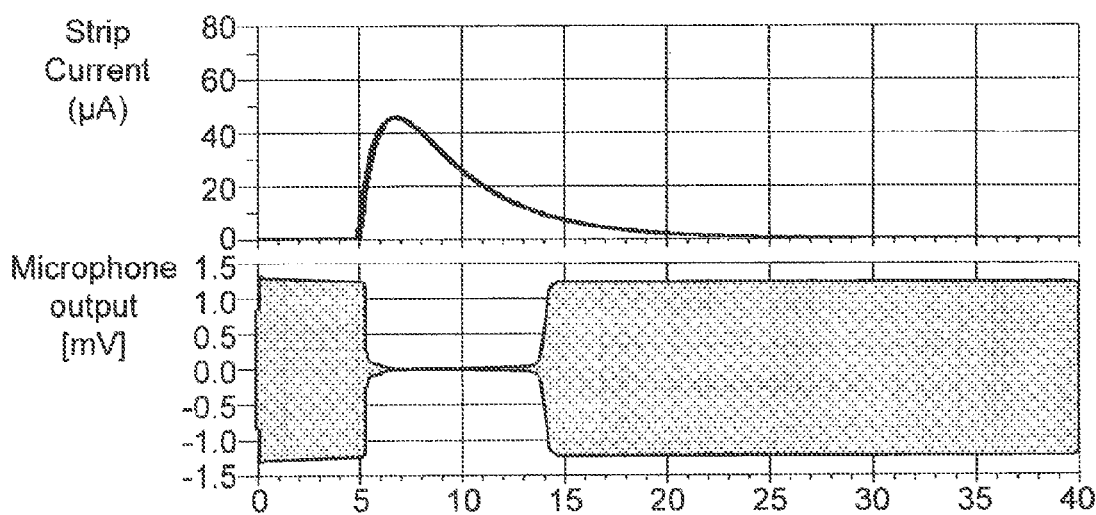
Figure 13C:
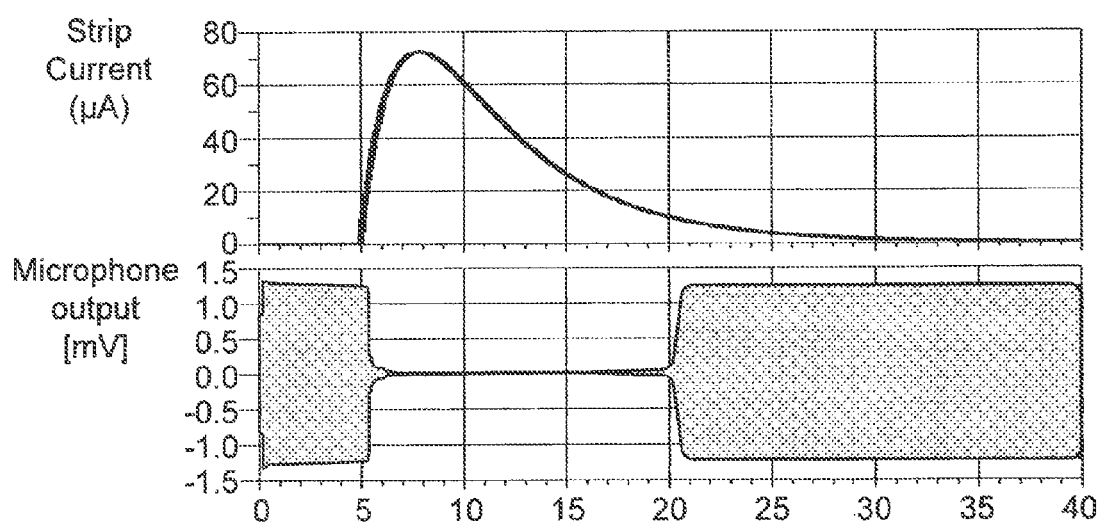

FIGS. 13A-C are graphic illustrations of a strip current (top part) and a microphone recorded waveform (bottom part) for three actual distinct glucose values 48 mg/dL (13A), 189 mg/dL (13B), and 393 mg/dL (13C) in accordance with variations of the present invention. It is clearly shown that when glucose level is higher, the time period in which the microphone waveform is shut down is getting longer (up to 15 sec).

It should be clear that the description of the embodiments and attached Figures set forth in this specification serves only for a better understanding of the invention, without limiting its scope. It should also be clear that a person skilled in the art, after reading the present specification could make adjustments or amendments to the attached Figures and above described embodiments that would still be covered by the present invention.

What is claimed is:
1. An apparatus comprising:
   a fluid monitoring apparatus comprising:
      a connecting plug configured to mate with an audio jack phone port,
         wherein the audio jack phone port has at least three audio pins;
      a first ring,
         wherein the first ring is positioned on the connecting plug, and
         wherein the first ring is configured to mate with a first audio pin of the audio jack phone port;
      a second ring,
         wherein the second ring is positioned on the connecting plug, and
         wherein the second ring is configured to mate with a second audio pin of the audio jack phone port; and
      a third ring,
         wherein the third ring is positioned on the connecting plug, and
         wherein the third ring is configured to mate with a third audio pin of the audio jack phone port;
         wherein at least one of the first, second, and third rings of the connection plug is configured to receive power for the fluid monitoring apparatus from the audio jack phone port;

wherein at least one of the first, second, and third rings of the connection plug is configured to receive data from the audio jack phone port; and wherein at least one of the first, second, and third rings of the connection plug is configured to transmit data from the fluid monitoring apparatus to the audio jack phone port.

2. The apparatus of claim 1, wherein the first ring is configured to receive power for the fluid monitoring apparatus from the audio jack phone port.

3. The apparatus of claim 1, wherein the first ring is configured to transmit data from the fluid monitoring apparatus to the audio jack phone port.

4. The apparatus of claim 1, wherein the first ring is configured to:
(i) receive power for the fluid monitoring apparatus from the audio jack phone port and
(ii) transmit data from the fluid monitoring apparatus to the audio jack phone port.

5. The apparatus of claim 1, wherein the second ring is configured to receive power for the fluid monitoring apparatus from the audio jack phone port.

6. The apparatus of claim 1, wherein the second ring is configured to transmit data from the fluid monitoring apparatus to the audio jack phone port.

7. The apparatus of claim 1, wherein the second ring is configured to:
(i) receive power for the fluid monitoring apparatus from the audio jack phone port and
(ii) transmit data from the fluid monitoring apparatus to the audio jack phone port.

8. The apparatus of claim 1, wherein the third ring is configured to receive power for the fluid monitoring apparatus from the audio jack phone port.

9. The apparatus of claim 1, wherein the third ring is configured to receive data from the audio jack phone port.

10. The apparatus of claim 1, wherein the third ring is configured to:
(i) receive power for the fluid monitoring apparatus from the audio jack phone port and
(ii) receive data from the fluid monitoring apparatus.

11. The apparatus of claim 1, wherein the first ring is configured to receive power for the fluid monitoring apparatus;
wherein the second ring is configured to receive data from the audio jack phone port; and
wherein the third ring is configured to transmit data from the fluid monitoring apparatus to the audio jack phone port.

12. The apparatus of claim 11, wherein the first audio pin comprises a left speaker output,
wherein the second audio pin comprises a right speaker output, and
wherein the third audio pin comprises a microphone input.

13. The apparatus of claim 1, wherein the first ring is configured to:
(i) receive power for the fluid monitoring apparatus and
(ii) receive data from the audio jack phone port;
wherein the second ring is configured to receive power for the fluid monitoring apparatus; and
wherein the third ring is configured to transmit data from the fluid monitoring apparatus to the audio jack phone port.

14. The apparatus of claim 13, wherein the first audio pin comprises a left speaker output,
wherein the second audio pin comprises a right speaker output, and
wherein the third audio pin comprises a microphone input.

* * * * *